US010202570B2

(12) United States Patent
Jinno et al.

(10) Patent No.: US 10,202,570 B2
(45) Date of Patent: Feb. 12, 2019

(54) BLADE TIP-PROVIDED MICROPIPETTE HOLDING APPARATUS AND INTRACYTOPLASMIC SPERM INJECTION METHOD

(71) Applicant: KITAZATO SCIENCE CO., LTD., Fuji-shi, Shizuoka (JP)

(72) Inventors: Masao Jinno, Chofu (JP); Futoshi Inoue, Fujinomiya (JP)

(73) Assignee: KITAZATO BIOSCIENCE CO., LTD., Fuji-Shi, Shuzuoka (JP)

( * ) Notice: Subject to any disclaimer, the term of this patent is extended or adjusted under 35 U.S.C. 154(b) by 85 days.

(21) Appl. No.: 15/349,631

(22) Filed: Nov. 11, 2016

(65) Prior Publication Data
US 2017/0121660 A1 May 4, 2017

Related U.S. Application Data

(63) Continuation of application No. PCT/JP2015/062816, filed on Apr. 28, 2015.

(30) Foreign Application Priority Data

May 12, 2014 (JP) .................................. 2014-098695

(51) Int. Cl.
  *C12M 3/00* (2006.01)
  *C12M 1/42* (2006.01)
  *A61B 17/43* (2006.01)
  *G02B 21/32* (2006.01)

(52) U.S. Cl.
  CPC ............. *C12M 23/48* (2013.01); *A61B 17/43* (2013.01); *C12M 21/06* (2013.01); *C12M 35/00* (2013.01); *G02B 21/32* (2013.01)

(58) Field of Classification Search
  CPC ............................ C12M 21/06; C12M 23/48
  See application file for complete search history.

(56) References Cited

U.S. PATENT DOCUMENTS

2005/0174085 A1 8/2005 Yuri
2006/0149280 A1 7/2006 Harvie et al.
(Continued)

FOREIGN PATENT DOCUMENTS

CN    101715552 A    5/2010
CN    103372472 A    10/2013
(Continued)

OTHER PUBLICATIONS

The extended European Search Report dated Nov. 28, 2017, by the European Patent Office in corresponding European Application No. 15792375.6. (7 pages).
(Continued)

*Primary Examiner* — Gautam Prakash
*Assistant Examiner* — Lydia Edwards
(74) *Attorney, Agent, or Firm* — Buchanan Ingersoll & Rooney PC

(57) ABSTRACT

A blade tip-provided micropipette holding apparatus has a tubular micropipette holder so constructed that a blade tip-provided micropipette to be inserted into a living cell can be mounted on a front-end portion thereof and a holder-holding device for holding the micropipette holder. The holder-holding device has a base member and a tubular rotating member which is rotatably held by the base member and into which the tubular micropipette holder can be penetrated. The tubular rotating member has holder position adjusting mechanisms each composed of a plurality of side holes formed on a side surface of the tubular rotating member at different positions of the side surface thereof in a circumferential direction thereof and holder position adjusting members each capable of entering into the tubular rotating member from the side holes and contacting an outer surface of the micropipette holder penetrating through the tubular rotating member.

12 Claims, 15 Drawing Sheets

(56) References Cited

U.S. PATENT DOCUMENTS

| | | | | |
|---|---|---|---|---|
| 2008/0213899 A1* | 9/2008 | Olgac | ............. | C12M 21/06 435/455 |
| 2009/0130743 A1 | 5/2009 | Miyawaki et al. | | |

FOREIGN PATENT DOCUMENTS

| | | |
|---|---|---|
| CN | 103389366 A | 11/2013 |
| JP | 58-040210 A | 3/1983 |
| JP | 5-185384 A | 7/1993 |
| JP | 2005-258413 A | 9/2005 |
| JP | 2007-006775 A | 1/2007 |
| JP | 2013-160960 A | 8/2013 |
| WO | 2008/063136 A1 | 5/2008 |

OTHER PUBLICATIONS

Shimachi et al., "Research on Micromanipulator Capable of Converting Posture of an Object," Nendo The Japan Society for Precision Engineering Shuki Taikai Gakujutsu Koenkai Koen Ronbunshu, 1990 (month unknown), pp. 857-858, with partial translation.

Nakao, et al., "Micro Handling with Rotational Needle-type Tools under Real Time Observation," CIRP Annals—Manufacturing Technology, 2001 (month unknown), pp. 9-12, vol. 50.

Notification of Transmittal of Translation of the International Preliminary Report on Patentability (Forms PCT/IB/338, PCT/IB/373 and PCT/ISA/237) dated Nov. 24, 2016, by the International Bureau of WIPO in corresponding International Application No. PCT/JP2015/062816. (7 pages).

International Search Report (PCT/ISA/210) dated Aug. 4, 2015, by the Japanese Patent Office as the International Searching Authority for International Application No. PCT/JP2015/062816.

Written Opinion (PCT/ISA/237) dated Aug. 4, 2015, by the Japanese Patent Office as the International Searching Authority for International Application No. PCT/JP2015/062816.

Office Action (Notification of Reasons for Refusal) dated May 15, 2018 by the Japanese Patent Office in corresponding Japanese Patent Application No. 2016-519203, and an English Translation of the Office Action. (6 pages).

* cited by examiner

BLADE TIP-PROVIDED MICROPIPETTE HOLDING APPARATUS AND INTRACYTOPLASMIC SPERM INJECTION METHOD

TECHNICAL FIELD

The present invention relates to a blade tip-provided micropipette holding apparatus which holds a micropipette for use in microinsemination and the like and is used for an operation of inserting the blade tip of micropipette into a living cell and an intracytoplasmic sperm injection method.

BACKGROUND ART

In the field of biotechnology, under microscopic observation, operations of injecting sperms and sperm cells into ova and nuclei, cytoplasms, and DNAs into cells are performed. A micromanipulation system to be used in these operations is proposed, as disclosed in Japanese Patent Application Laid-Open Publication No. 2005-258413 (patent document 1). Under microscopic image observation, a micromanipulator is used in operating a micro-needle (blade tip-provided micropipette) to perform genetic recombination and microinsemination operations for test objects.

An ICSI (intracytoplasmic sperm injection method) in the microinsemination is used as an assisted reproductive technology (ART) to treat a case in which a man has a severe defect in his semen found as a result of diagnosis and observation. The microinsemination is a method of performing the entire process in vitro from the run-up of the sperm through a female genital track, the fertilization of the sperm with the ovum, and the fusion between the ovum and the sperm. The in vitro fertilization allows fertilization even in a case where the number of sperms in ejaculated semen is extremely few and a case where the sperm in the semen lacks in the ability of entering into the ovum (fertilizing ability) by itself.

In the ICSI (intracytoplasmic sperm injection method), it is necessary to directly inject the sperm into the cytoplasm inside the ovum. To this end, it is necessary for a blade tip-provided micropipette to pierce through the zona pellucid of the ovum and the egg membrane and reach into the cytoplasm. Although it is comparatively easy for a blade tip of the micropipette to pierce through the zona pellucid of the ovum, it is not easy for the blade tip to pierce through the egg membrane. This is because the egg membrane is deformed and hardened by the contact therebetween.

A vibration-type microinjection apparatus is disclosed in Japanese Patent Application Laid-Open Publication No. 2007-6775 (patent document 2). The vibration-type microinjection apparatus of the patent document 2 has the vibrator 28 having the housing which is connected in series to the micropipette 8 and on which the piezoelectric actuator 29 is mounted and the signal adjusting device 21 for adjusting electric signals applied to the piezoelectric actuator 29. By inputting the electric signals to the piezoelectric actuator 29, vibrations are axially imparted to the micropipette 8 through the vibrator 28 having the housing.

PRIOR ART DOCUMENTS

Patent Documents

Patent document 1: Japanese Patent Application Laid-Open Publication No. 2005-258413
Patent document 2: Japanese Patent Application Laid-Open Publication No. 2007-6775

SUMMARY OF THE INVENTION

Problems to be Solved by the Invention

According to the vibration-type microinjection apparatus of the patent document 2, the blade tip can be pierced favorably to some extent through membranes of the ovum to be fertilized including the zone pellucid, the cell membrane, and the nuclear membrane having different properties. But there is a demand for the development of an apparatus allowing the blade tip of the micropipette to pierce into the cytoplasm of the ovum more simply and more securely than before.

It is an object of the present invention to provide a blade tip-provided micropipette holding apparatus allowing a blade tip-provided micropipette to pierce through the cytoplasm and membrane of the ovum and reach into the cytoplasm easily and securely and an intracytoplasmic sperm injection method.

Means for Solving the Problems

The means for achieving the above-described object is as described below.

A blade tip-provided micropipette holding apparatus comprising a tubular micropipette holder and a holder-holding device for holding said micropipette holder; wherein said tubular micropipette holder is constructed that a blade tip-provided micropipette can be mounted on a front-end portion thereof; said holder-holding device has a base member and a tubular rotating member which is rotatably held by said base member and into which said tubular micropipette holder can be penetrated; and said tubular rotating member has a holder position adjusting mechanism comprising a plurality of side holes formed on a side surface of said tubular rotating member at different positions in a circumferential direction thereof and holder position adjusting members each capable of entering into said tubular rotating member from said side holes and contacting an outer surface of said micropipette holder penetrating through said tubular rotating member.

Another means for achieving the above-described object is as described below.

An intracytoplasmic sperm injection method of the present invention includes a step of holding an ovum by a suction pipette; a step of bringing a front-end portion of a micropipette having a blade tip at a front end thereof and accommodating a sperm therein into contact with an ovum held by the suction pipette; a step of moving the micropipette forward and inserting the blade tip into an egg zona pellucid; a step of bringing the blade tip into contact with an egg membrane of the ovum and pressing the egg membrane by means of the blade tip; a step of rotating the micropipette to rotate a blade surface of the blade tip so that the blade tip pierces through the egg membrane and enters into a cytoplasm; and a step of releasing the sperm accommodated inside the micropipette in an interior of the cytoplasm.

MODE FOR CARRYING OUT THE INVENTION

Figure 1:
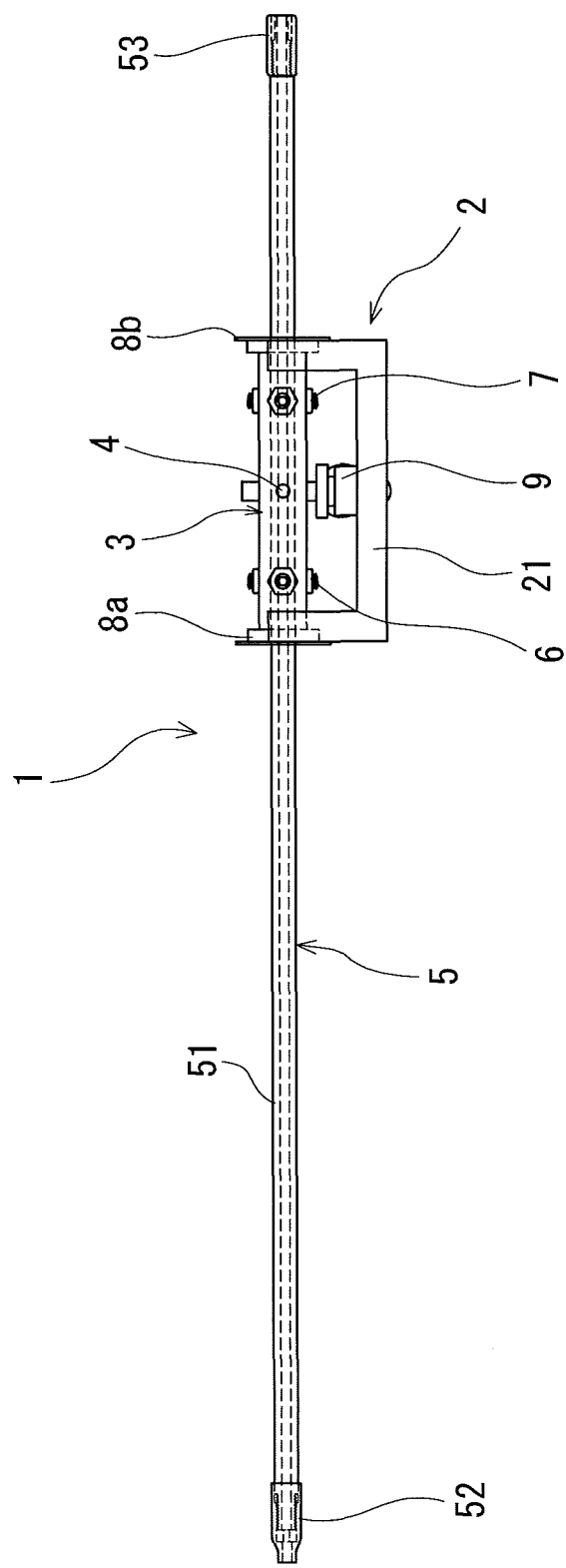
FIG. 1 is a front view of an embodiment of a blade tip-provided micropipette holding apparatus of the present invention.
Figure 2:
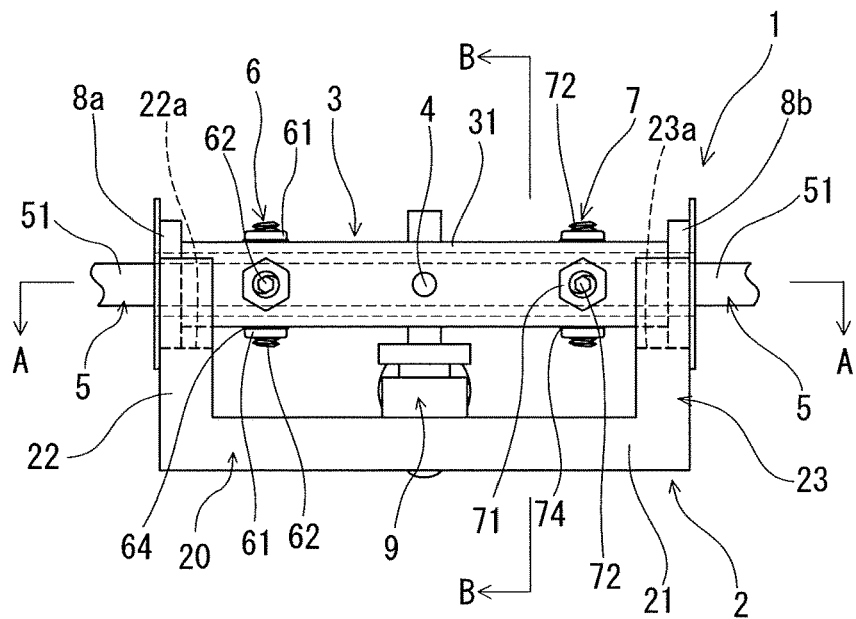
FIG. 2 is an enlarged front view of a holder-holding device of the blade tip-provided micropipette holding apparatus shown in FIG. 1.
Figure 3:
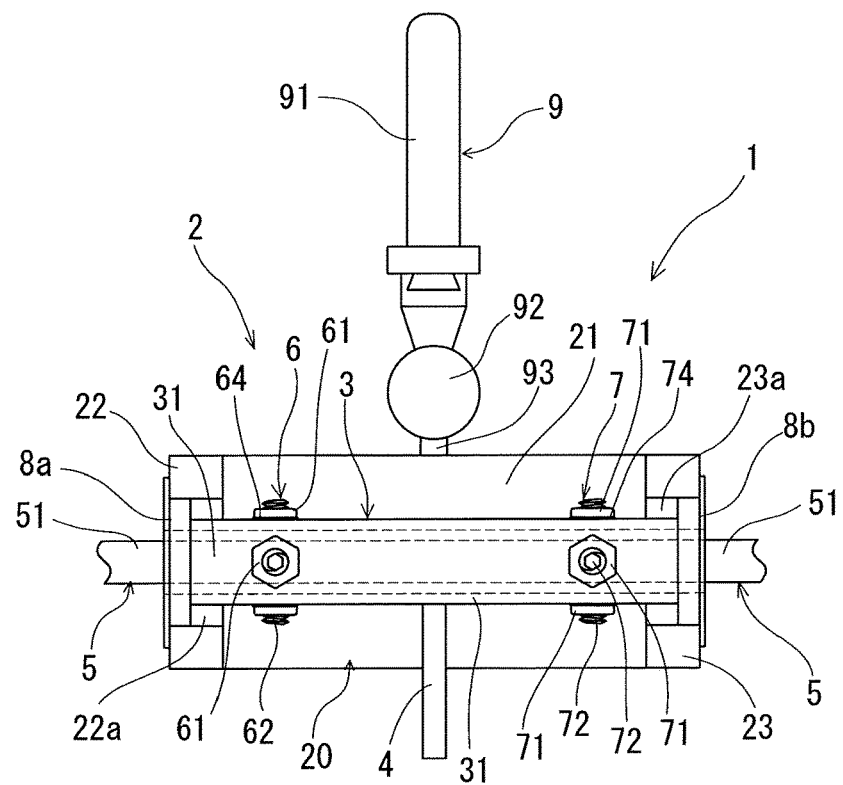
FIG. 3 is an enlarged plan view of the holder-holding device of the blade tip-provided micropipette holding apparatus shown in FIG. 1.
Figure 4:
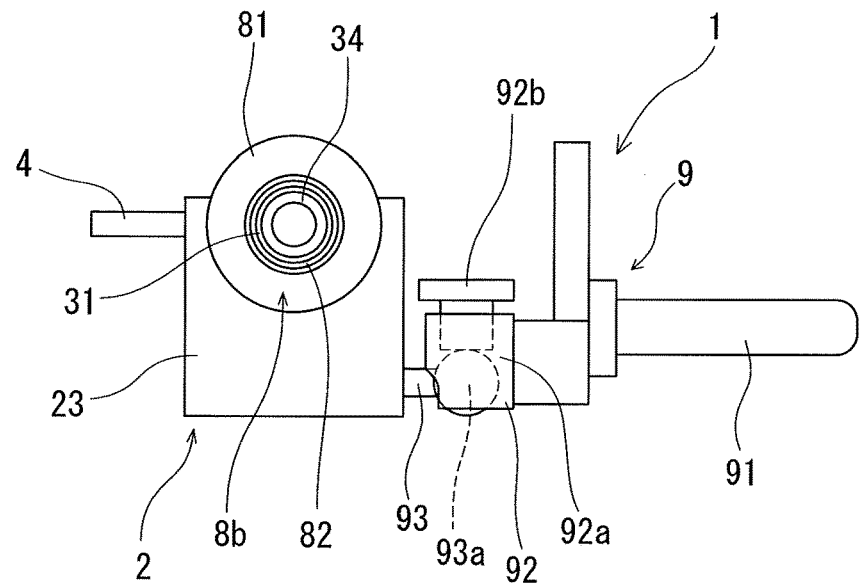
FIG. 4 is an enlarged right side view of the holder-holding device part of the blade tip-provided micropipette holding apparatus shown in FIG. 1

A blade tip-provided micropipette holding apparatus of the present invention is described below by using embodiments shown in the drawings.

A blade tip-provided micropipette holding apparatus 1 of the present invention has a tubular micropipette holder 5 so constructed that a blade tip-provided micropipette 15 to be inserted into a living cell (for example, ovum, nucleus transferred cell) can be mounted on a front-end portion thereof and a holder-holding device 2 for holding the micropipette holder 5. The holder-holding device 2 has a base member 20 and a tubular rotating member 3 which is rotatably held by the base member 20 and into which the tubular micropipette holder 5 can be penetrated. The tubular rotating member 3 has holder position adjusting mechanisms 6, 7 each composed of a plurality of side holes 35 formed on a side surface of the tubular rotating member 3 at different positions of the side surface thereof in a circumferential direction thereof and holder position adjusting members 62, 72 each capable of entering into the tubular rotating member 3 from the side holes 35 and contacting an outer surface of the micropipette holder 5 which has been penetrated through the tubular rotating member 3.

The micropipette holding apparatus 1 of the present invention is described below by using an embodiment in which the micropipette holding apparatus 1 is applied to a micropipette holding apparatus for holding a micropipette for use in microinsemination.

As shown in FIGS. 1 through 6, the blade tip-provided micropipette holding apparatus 1 of the present invention has the tubular micropipette holder 5 and the holder-holding device 2 for holding the micropipette holder 5.

As shown in FIGS. 1, 7 through 9, the tubular micropipette holder 5 has a tubular main body 51, a front-end side ring-shaped member 52 provided at a front-end portion of the tubular main body 51, a proximal-end side ring-shaped member 53 provided at a proximal-end side of the tubular main body 51, and a tubular elastic member 54 accommodated inside the front-end side ring-shaped member 52 and pressed by the front-end side ring-shaped member 52 and the front end of the tubular main body 51.

The tubular main body 51 is a tubular body having an inner diameter larger than an outer diameter of the micropipette 15 and has a lumen 56 penetrating therethrough from its front end to proximal end. At a front-end portion of the tubular main body 51, there is formed a male screw portion threadedly engageable with a female screw portion formed on an inner surface of the front-end side ring-shaped member 52. The front-end portion of the tubular main body 51 constitutes a portion for holding a proximal-end portion of the micropipette 15. The tubular elastic member 54 accommodated inside the front-end side ring-shaped member 52 allows a proximal-end portion of the micropipette 15 to penetrate therethrough and can be pressed between the front end of the tubular main body 51 and a proximal end of a small inner diameter portion of the front-end side ring-shaped member 52. By being pressed, the inner diameter of tubular elastic member 54 decreases and is capable of holding the proximal-end portion of the micropipette 15 with the tubular elastic member 54 in close contact with the proximal-end portion of the micropipette.

Figure 21:
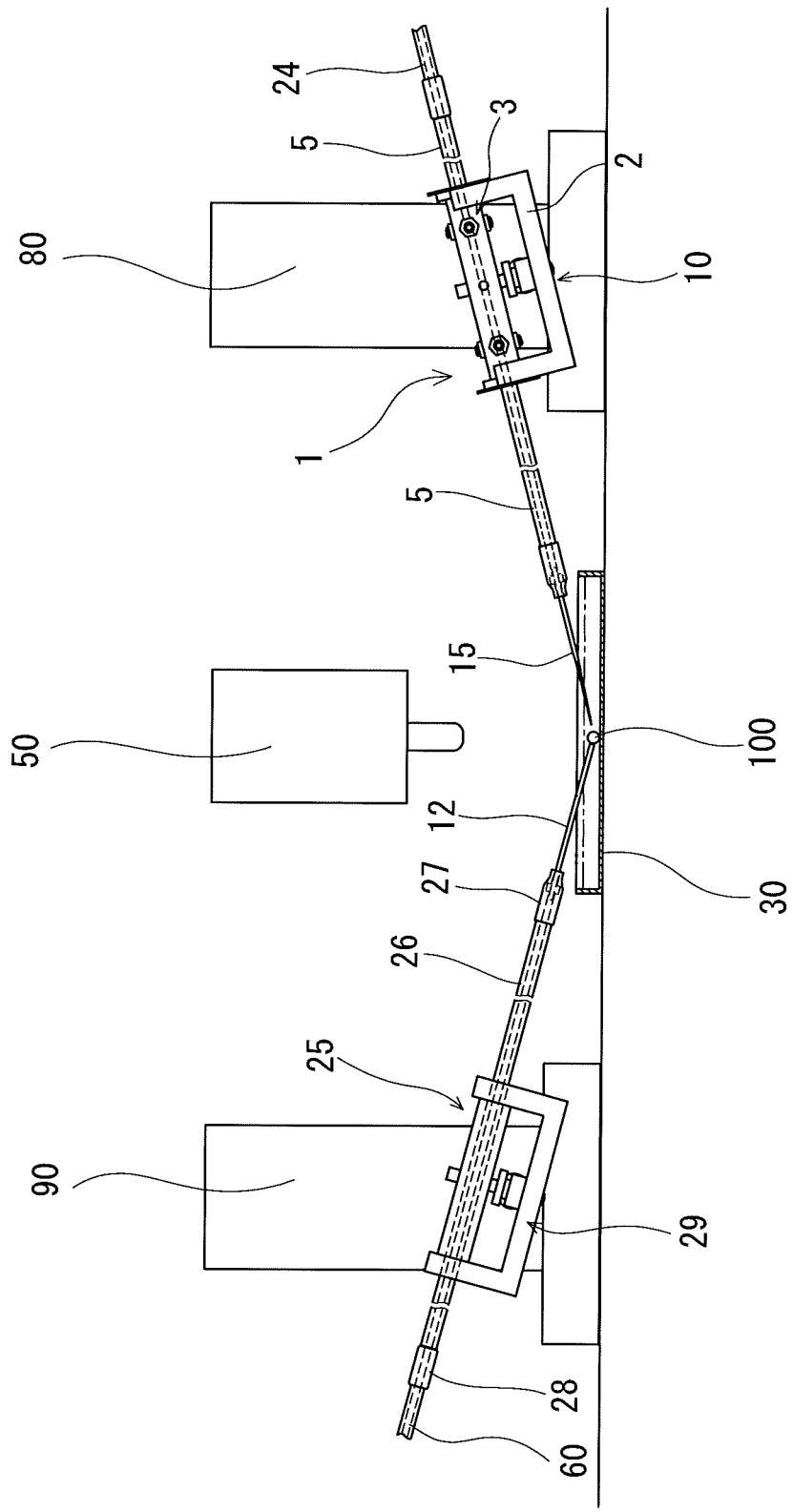
FIG. 21 is an explanatory view for explaining the intracytoplasmic sperm injection method of the present invention.

At a rear end portion of the tubular main body 51, the tubular main body 51 has a small-diameter proximal-end portion which is disposed at the most proximal end and has a smaller outer diameter and a male screw portion extended forward from the small-diameter proximal-end portion. The proximal-end side ring-shaped member 53 has an encapsulating portion for the above-described small-diameter proximal-end portion and a female screw portion which is formed on an inner surface of the proximal-end side ring-shaped member 53 and is threadedly engageable with the above-described male screw portion. As shown in FIG. 21, the small-diameter proximal-end portion constitutes a connecting portion of a tube 24 for flowing a gas or a liquid to be sucked into the micropipette 15 and discharged therefrom.

The blade tip-provided micropipette 15 to be mounted on the tubular micropipette holder 5 is a hollow needle having an internal passage 19 communicable with the inside of the tubular main body 51 and penetrating through the blade tip-provided micropipette from its front end to proximal end and having a blade tip 18 at the front end thereof. The micropipette 15 shown in FIG. 9 has a small-diameter portion 17 extended in a predetermined length toward the proximal-end side thereof from the blade tip 18 and a body portion 16 extended from a proximal end of the small-diameter portion 17 to the rear end of the micropipette. The blade tip has a blade surface formed by cutting the blade tip diagonally to the central axis of the micropipette. As the blade tip-provided micropipette 15, a transparent needle made of glass is normally used.

In the blade tip-provided micropipette holding apparatus 1 of this embodiment, the holder-holding device 2 has the base member 20 and the tubular rotating member 3 which is rotatably held by the base member 20 and through which the tubular micropipette holder 5 can be penetrated.

As shown in FIGS. 2 through 6, the base member 20 has a base portion 21, two side plate portions 22, 23 erect from the base portion 21, and ball bearings 8a, 8b fixed to the side plate portions 22, 23 respectively. The base portion 21 is a plate-shaped portion formed rectangularly. The side plate portions 22, 23 are erect from both side edge portions of the base portion with the side plate portions being opposed to each other. The side plate portions 22, 23 are formed almost parallel with each other and equally in the heights thereof. The side plate portions 22, 23 have concave portions 22a, 23a formed on an upper portion thereof respectively.

Figure 5:
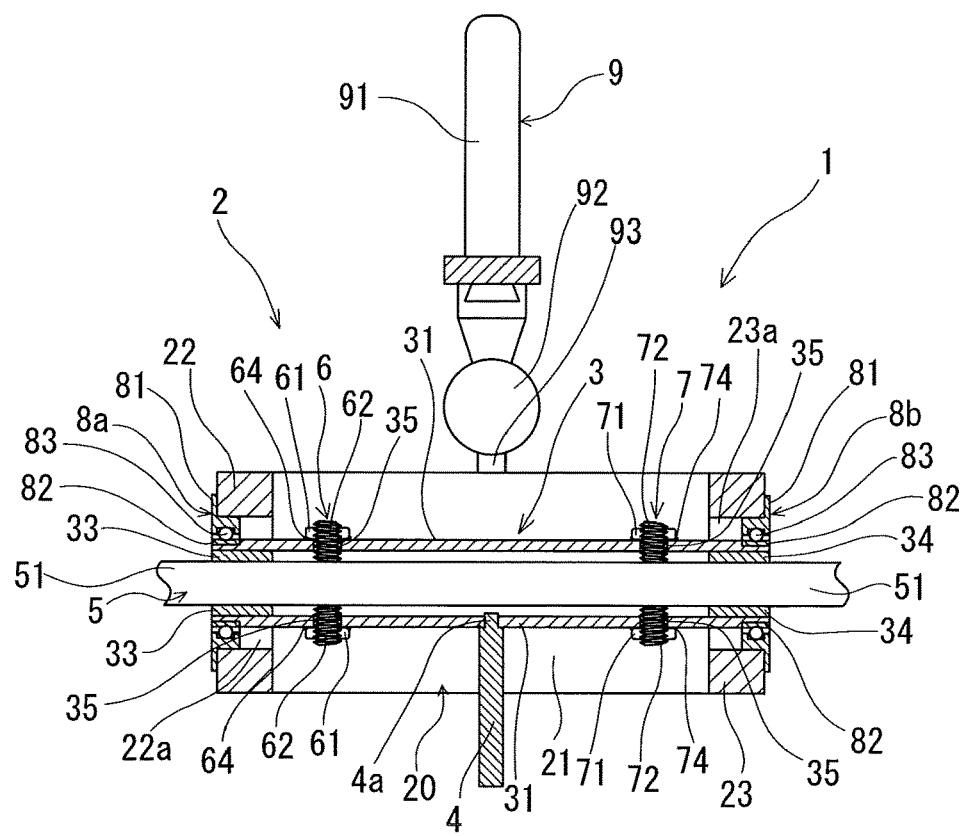
FIG. 5 is a sectional view taken along a line A-A of FIG. 2.

As shown in FIGS. 1 through 6, the tubular rotating member 3 has the ball bearing 8a fixed to one end of a tubular body 31 and the ball bearing 8b fixed to the other end thereof. As shown in FIG. 5, each of the ball bearings 8a, 8b has an outer ring-shaped member 81, an inner ring-shaped member 82, and a plurality of ball bodies disposed on the two ring-shaped members. The inner ring-shaped member 82 of the ball bearing 8a is fixed to one end of the tubular body 31, while the inner ring-shaped member 82 of the ball bearing 8b is fixed to the other end of the tubular body 31. The tubular body 31 having the ball bearings 8a, 8b at its both ends is mounted on the concave portions 22a, 23a of the side plate portions 22, 23 of the base member 20 at the ball bearings.

More specifically, the outer ring-shaped members 81 of the ball bearings 8a, 8b are mounted on the concave portions 22a, 23a of the side plate portions 22, 23 of the base member 20 respectively. Thereby the tubular body 31 is rotatably held between the side plate portions 22, 23 of the base member 20. Each of the outer ring-shaped members 81 of the ball bearings 8a, 8b has a flange portion having an outer diameter larger than the inner diameter of the concave portions formed on the side plate portions 22, 23 respectively. The flange portion is so constructed as to contact an outer side surface of each of the side plate portions 22, 23. Thereby the tubular body 31 on which the ball bearings 8a, 8b are mounted is prevented from moving.

The tubular rotating member 3 has holder position adjusting mechanisms 6, 7 each composed of a plurality of side holes 35 formed on the side surface of the tubular body 31 (tubular rotating member 3) at different positions of the side surface thereof in the circumferential direction thereof and the holder position adjusting members 62, 72 each capable of entering into the tubular rotating member 3 from the side holes 35 and contacting the outer surface of the micropipette holder 5 which has been penetrated through the tubular rotating member 3.

Because the blade tip-provided micropipette holding apparatus 1 of the present invention has the above-described holder position adjusting mechanisms, by adjusting the holder position adjusting mechanisms 6, 7 with the blade tip-provided micropipette 15 being mounted on the micropipette holder 5, it is possible to adjust the central axis of the front-end portion of the micropipette to be approximately centered during the rotation of the tubular rotating member 3. Therefore it is possible to preferably rotate the blade surface of the blade tip of the micropipette.

In the micropipette holding apparatus 1 of this embodiment, the tubular rotating member 3 has the first holder position adjusting mechanism 6 and the second holder position adjusting mechanism 7 spaced at a predetermined interval from the first holder position adjusting mechanism 6. Although it is preferable to provide the tubular rotating member 3 with these two holder position adjusting mechanisms 6, 7, the tubular rotating member may be provided with one holder position adjusting mechanism.

The holder position adjusting mechanism 6 is constructed of a plurality of the side holes (specifically, four) 35 formed on the tubular body 31 at almost the same position thereof in the axial direction thereof, a plurality of male screw members 62 constituting the holder position adjusting members respectively, and a plurality female screw portions 61 which are formed in the vicinity of the side holes 35 and threadedly engageable with the male screw members 62 respectively. In this embodiment, the four side holes 35 are formed at intervals of an almost equal angle (specifically, at intervals of 90 degrees) with respect to the central axis of the tubular body 31.

As in the case of the holder position adjusting mechanism 6, the holder position adjusting mechanism 7 is constructed of a plurality of the side holes (specifically, four) 35 formed on the tubular body 31 at almost the same position thereof in the axial direction thereof, a plurality of male screw members 72 constituting the holder position adjusting members respectively, and a plurality female screw portions 71 which are formed in the vicinity of the side holes 35 and threadedly engageable with the male screw members 72 respectively. In this embodiment, the four side holes 35 are formed at intervals of an almost equal angle (specifically, at intervals of 90 degrees) with respect to the central axis of the tubular body 31.

Figure 6:
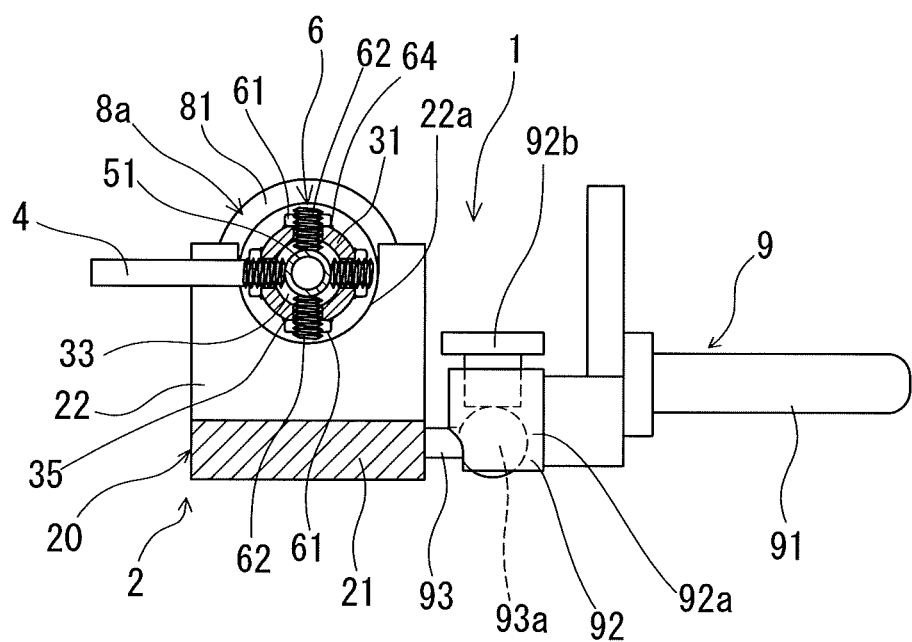
FIG. 6 is a sectional view taken along a line B-B of FIG. 2
Figure 7:
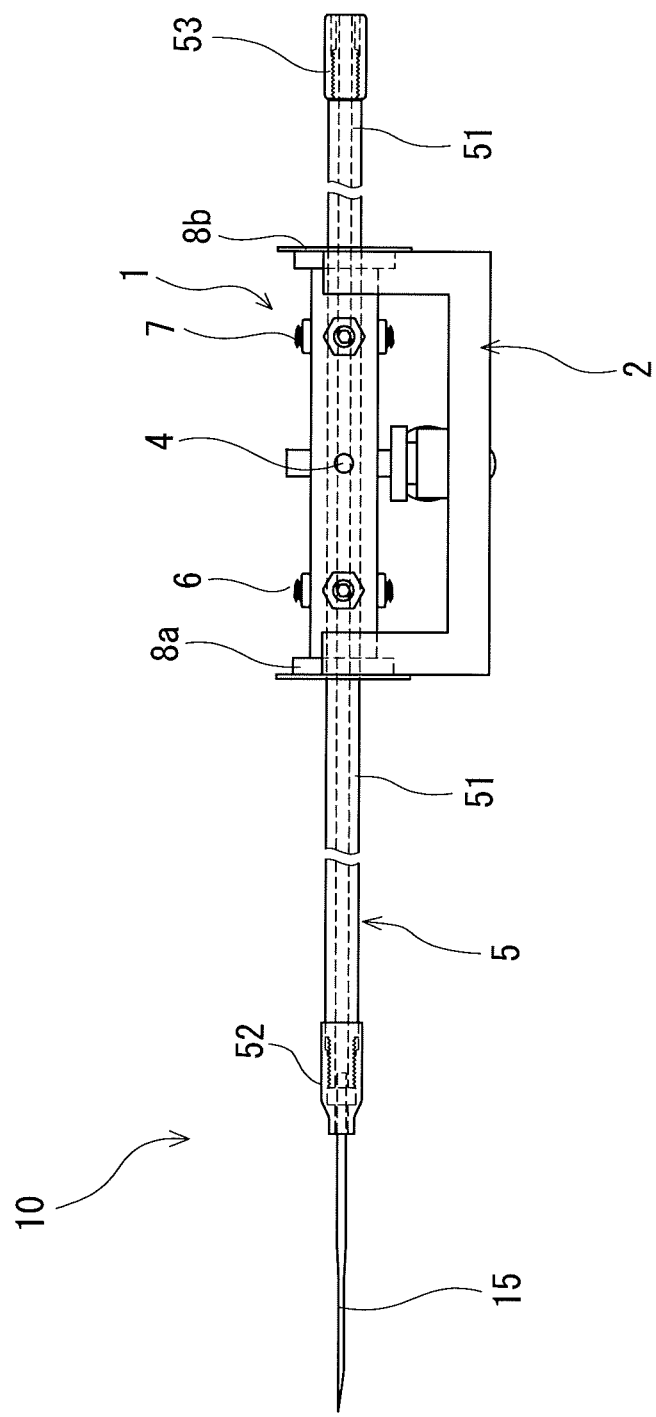
FIG. 7 is a partly abbreviated front view showing a state in which a blade tip-provided micropipette is mounted on the blade tip-provided micropipette holding apparatus of the present invention.
Figure 8:
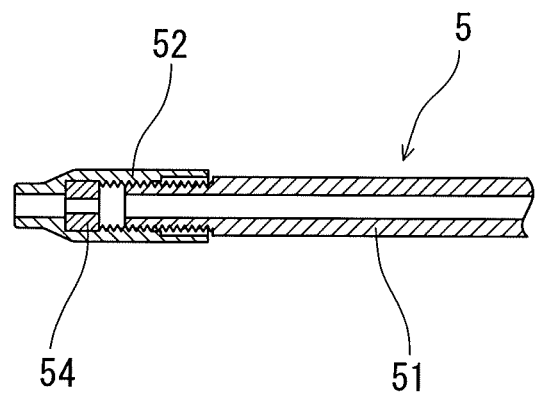
FIG. 8 is an enlarged sectional view of a front-end portion of a micropipette holder for use in the blade tip-provided micropipette holding apparatus of the present invention.
Figure 9:
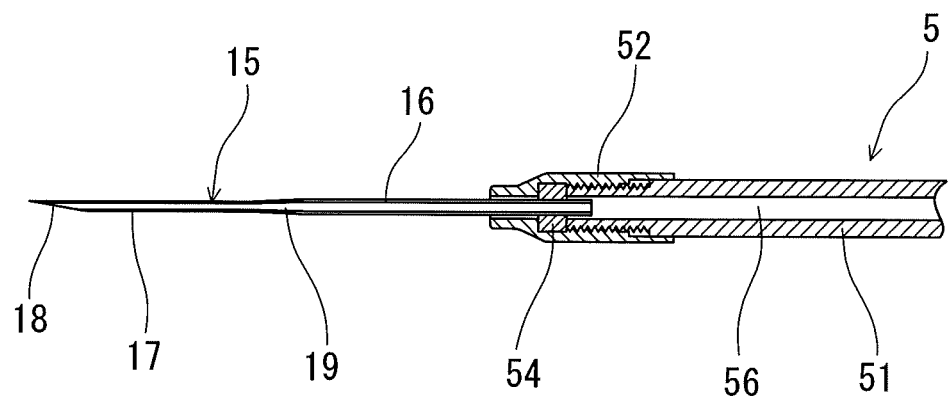
FIG. 9 is an enlarged sectional view of the blade tip-provided micropipette and a front-end portion of the micropipette holder shown in FIG. 7.

As the female screw portions 61, 71, nuts are used. The nuts are disposed on an outer surface of the tubular body 31 in such a way that internal female screw portions of the nuts are disposed above the side holes 35 and are fixed to the tubular body 31 by means of fixing portions (specifically, welding portions) 64, 74. By threadedly engaging the male screw portions 62, 72 respectively with the female screw portions (nuts) 61, 71 fixed to the tubular body 31, the front-end portions of the male screw portions penetrate through the female screw portions (nuts) 61, 71 and the side hole 35 and are capable of reaching the inside of the tubular body 31. As shown in FIG. 6, each of the male screw portions 62, 72, serving as the holder position adjusting members, which have arrived at the inside of the tubular body 31 is capable of contacting the outer surface of the micropipette holder 5 which has been penetrated through the tubular body 31.

By adjusting the projected length of each of the male screw portions 62, 72 inside the tubular body 31, it is possible to finely adjust the position of the micropipette holder 5 inside the tubular body 31 through which the micropipette holder 5 has been penetrated. For example, by adjusting the projected length of each of the two male screw portions 62 vertically opposed to each other as shown in FIG. 6, it is possible to adjust a vertical position of the micropipette holder 5 inside the tubular body 31. By adjusting the projected length of each of the two male screw portions 62 longitudinally opposed to each other as shown in FIG. 6, it is possible to adjust a horizontal position of the micropipette holder 5 inside the tubular body 31.

In the micropipette holding apparatus 1 of this embodiment, the tubular rotating member 3 has an operation projected portion 4 for manually rotating the tubular rotating member 3. More specifically, the tubular rotating member 3 has the rotation operation projected portion 4 provided on the side surface of the tubular body 31. A front-end portion 4a of the rotation operation projected portion 4 is inserted into a through-hole formed on the side surface of the tubular body 31 and fixed thereto. As the rotation operation projected portion, a rod-like body such as a round rod or a square pillar is preferable. By gripping the rotation operation projected portion 4, the tubular rotating member 3 (tubular body 31) can be easily rotated. As the rotation of the rotation operation projected portion 4 proceeds, it contacts the base portion 21 of the base member 20. Therefore in the micropipette holding apparatus 1 of this embodiment, the tubular rotating member 3 is incapable rotating 360 degrees. Thus the rotation operation projected portion 4 functions as a member for regulating the rotation angle of the tubular rotating member 3.

In the micropipette holding apparatus 1 of this embodiment, the tubular rotating member 3 has elastic tubular members 33, 34 accommodated inside one end side and other end side of the tubular body 31. The elastic tubular members 33, 34 are capable of closely contacting the micropipette holder 5 and allow the micropipette holder to be penetrated therethrough. The elastic members 33, 34 allow the micropipette holder 5 to be held by the tubular rotating member 3 (tubular body 31) without the micropipette holder 5 being shaken. The micropipette holder 5 penetrates through the tubular body 31 with both end portions of the micropipette holder 5 projecting from the tubular body 31. Thereby the holder-holding device 2 holds the micropipette holder 5 and the holder-holding device 2 is fitted on intermediate portions of the micropipette holder 5.

The micropipette holding apparatus 1 of this embodiment has a mounting part 9 which is mounted on the base member 20 and used to install the micropipette holding apparatus on a manipulator apparatus.

The mounting part 9 has a mounting body portion 91 formed in a rod-like configuration, a mounting portion 93 to be mounted on the base member 20, and a ball joint portion 92 connecting the mounting body portion 91 and the mounting portion 93 to each other. The ball joint portion 92 is constructed of a ball bearing 92a disposed at the side of the mounting body portion, a ball joint 93a disposed at an end portion of the mounting portion 93, and a fixing adjusting member 92b. By loosening the fixing adjusting member 92b, it is possible to alter the angle of the mounting body portion 91 with respect to the ball joint 93a (base portion 21 of base member 20). After altering the angle of the mounting body portion 91 to a desired angle, the fixing adjusting member 92b is tightened. Thereby it is possible to keep the mounting body portion 91 in an angle-altered state.

Figure 10:
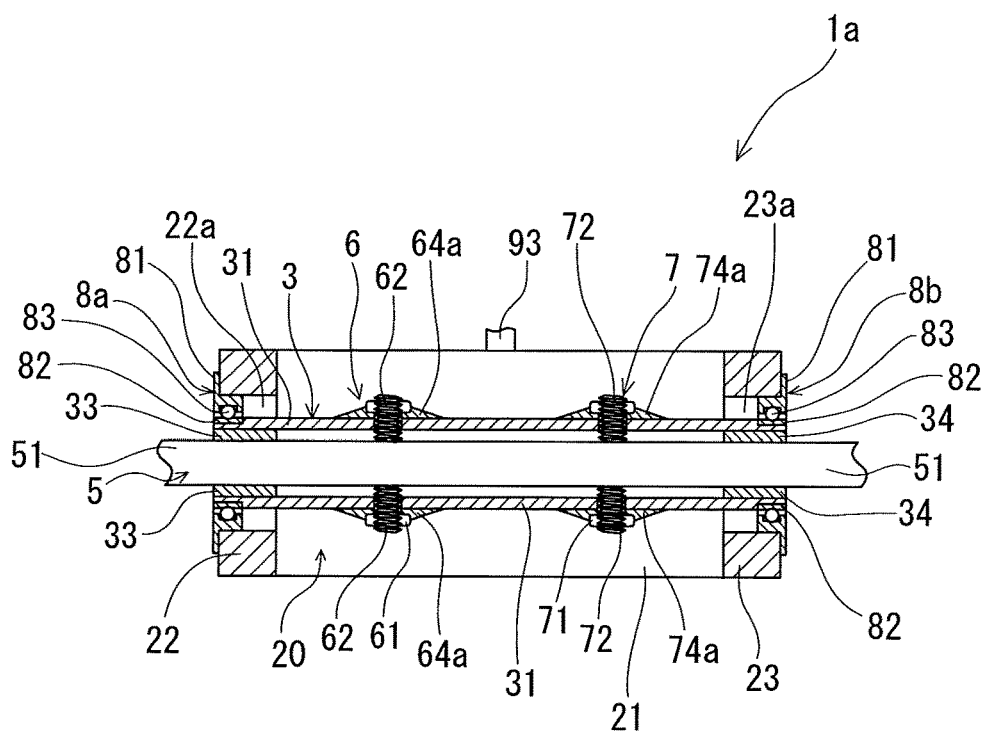
FIG. 10 is an enlarged sectional view of a holder-holding device of a blade tip-provided micropipette holding apparatus of another embodiment of the present invention.

In the micropipette holding apparatus of the above-described embodiment, as the form of fixing the female screw portion (nut) 61 to the tubular body 31, like the fixing form adopted in a micropipette holding apparatus 1a of an embodiment shown in FIG. 10, the female screw portion (nut) 61 may be fixed to the tubular body by means of adhesive members 64a, 74a provided on the outer surface of the tubular body 31. In the micropipette holding apparatus 1a of this embodiment, the tubular body 31 is provided with the adhesive members 64a, 74a surrounding the side holes and having a certain degree of thickness. The female screw portions (nuts) 61, 71 are buried in the adhesive members 64a, 74a to some extent. In this embodiment, the female screw portions (nuts) 61, 71 do not substantially contact the outer surface of the tubular body 31. Thus in the micropipette holding apparatus 1a of this embodiment, the holder position adjusting mechanisms 6, 7 are constructed of the side holes 35, the female screw portions (nuts) 61, 71, the male screw portions 62, 72, and the adhesive members 64a, 74a.

Figure 11:
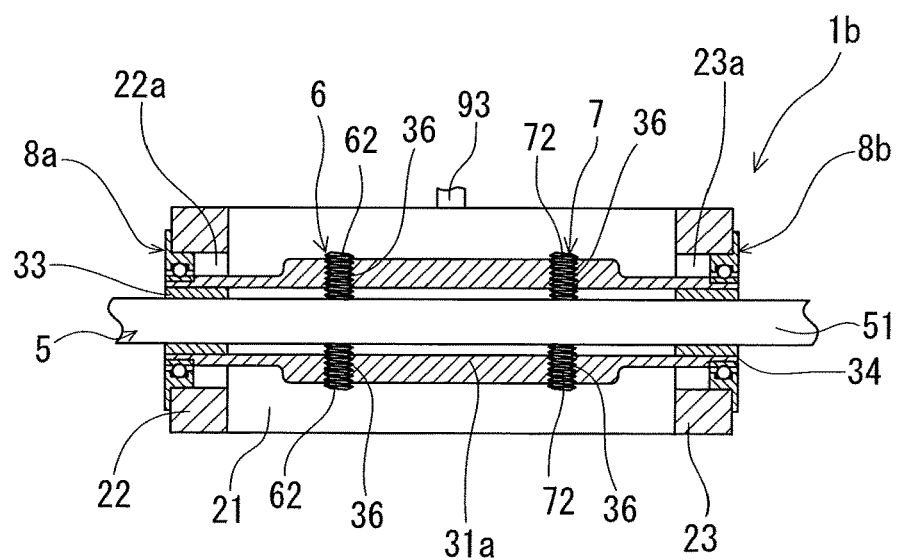
FIG. 11 is an enlarged sectional view of a holder-holding device of a blade tip-provided micropipette holding apparatus of another embodiment of the present invention.

In the micropipette holding apparatuses of the above-described embodiments, like a micropipette holding apparatus 1b of an embodiment shown in FIG. 11, the form of forming the female screw portion on the tubular body 31 may be so constructed that the nut is not formed on the outer surface of a tubular body 31a and that female screw portions 36 which threadedly engage the male screw portions 62, 72 are formed on inner surfaces of side holes of a tubular body 31a. In this embodiment, at least a central portion of the tubular body 31a is formed as a thick portion having a predetermined thickness. The side holes are formed on the thick portion. Therefore each of the side holes has a predetermined vertical length. The female screw portions 36 are formed on the inner surfaces of the respective side holes. Thus in the micropipette holding apparatus 1b of this embodiment, the holder position adjusting mechanisms 6, 7 are constructed of the side holes 35 having the female screw portions formed on the inner surfaces thereof and the male portions 62, 72 and do not have nuts and fixing portions.

Figure 12:
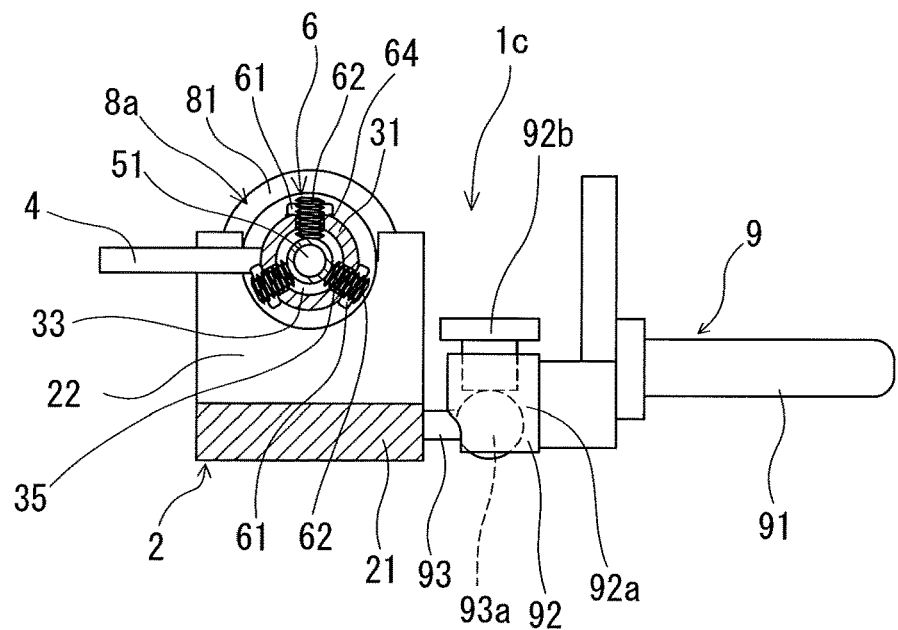
FIG. 12 is an enlarged sectional view of a holder-holding device of a blade tip-provided micropipette holding apparatus of another embodiment of the present invention.

In the micropipette holding apparatuses of the above-described all embodiments, like a micropipette holding apparatus 1c of an embodiment shown in FIG. 12, the side hole, the female screw portion (nut), and the male screw portion may be constructed of a plurality of (specifically, three) side holes 35 formed at almost the same position of the tubular body 31 in the axial direction thereof, a plurality of male screw portions 62 constructing the holder position adjusting member respectively, and a plurality of the female screw portions 61 which are disposed in the vicinity of the side holes 35 and engageable with the male screw portions 62 respectively. In this embodiment, the three side holes 35 are formed at intervals of almost an equal angle (specifically, at intervals of 120 degrees) with respect to the central axis of the tubular body 31.

Figure 13:
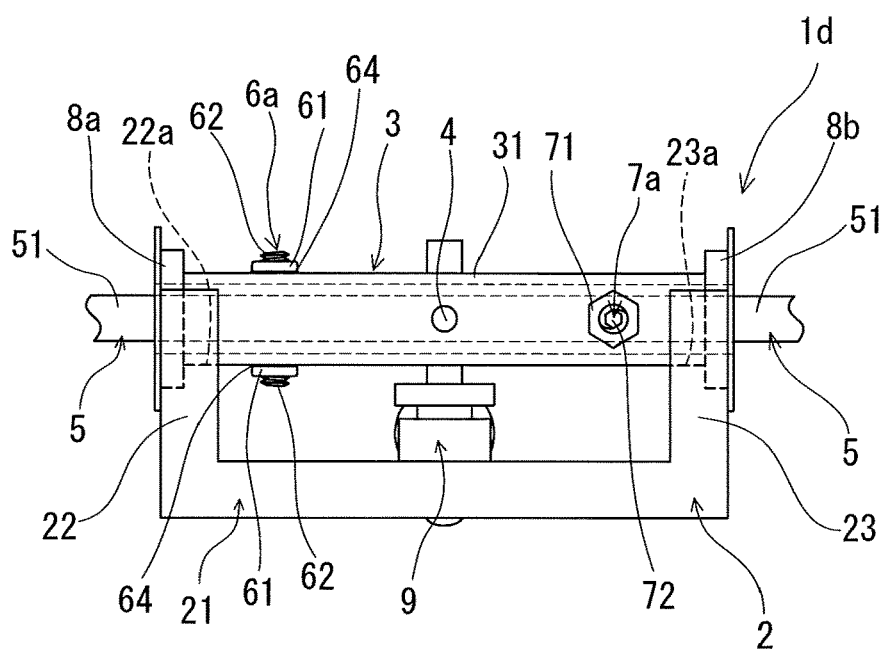
FIG. 13 is an enlarged front view of a holder-holding device of a blade tip-provided micropipette holding apparatus of another embodiment of the present invention.
Figure 14:
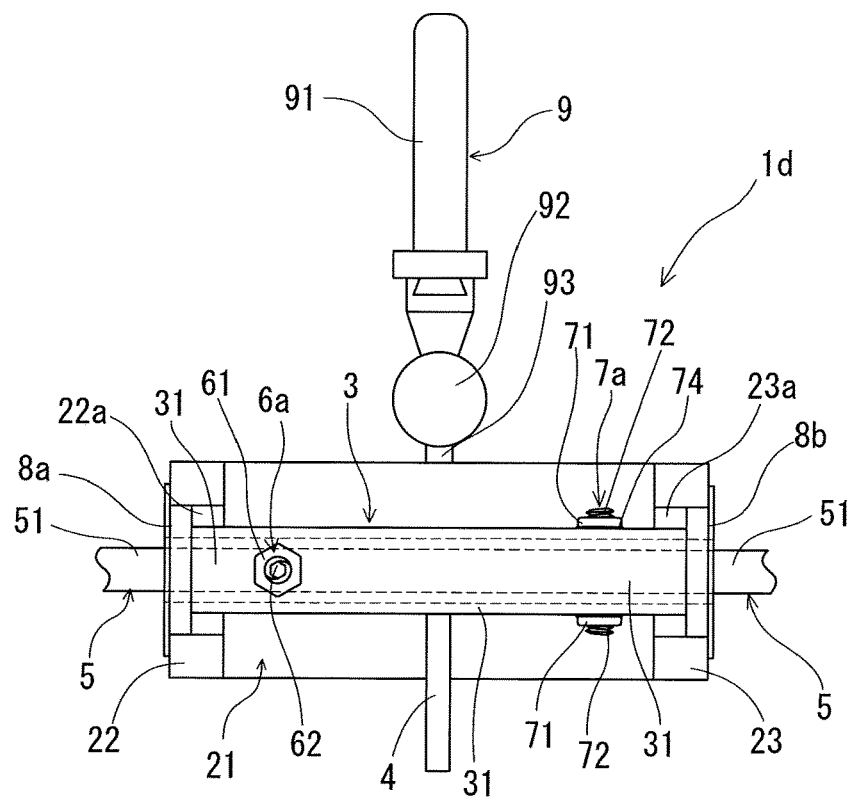
FIG. 14 is an enlarged plan view of the holder-holding device of the blade tip-provided micropipette holding apparatus shown in FIG. 13.

In the micropipette holding apparatuses of the above-described all embodiments, the side hole, the female screw portion (nut), and the male screw portion may be formed like those of a micropipette holding apparatus 1d of an embodiment shown in FIGS. 13 and 14. The micropipette holding apparatus 1d has a first holder position adjusting mechanism 6a constructed of two opposed side holes formed at almost the same position of the tubular body 31 in the axial direction thereof, male screw portions 62 constructing two holder position adjusting members, and two female screw portions 61 which are disposed in the vicinity of the side holes and engageable with the male screw portions 62 respectively and a second holder position adjusting mechanism 7a constructed of two opposed side holes spaced at almost 90 degrees from the two side holes of the first holder position adjusting mechanism 6a with respect to the central axis of the tubular body 31 and spaced apart therefrom by a predetermined interval, male screw portions 72 constructing two holder position adjusting members, and two female screw portions 71 which are disposed in the vicinity of the side holes and engageable with the male screw portions 72 respectively.

In the micropipette holding apparatus 1d of this embodiment, the first holder position adjusting mechanism 6a is capable of adjusting a vertical position of the micropipette holder 5 inside the tubular body 31, shown in FIG. 13, through which the micropipette holder has been penetrated. The second holder position adjusting mechanism 7a is capable of adjusting a horizontal position of the micropipette holder 5 inside the tubular body 31, shown in FIG. 13, through which the micropipette holder has been penetrated.

Figure 15:
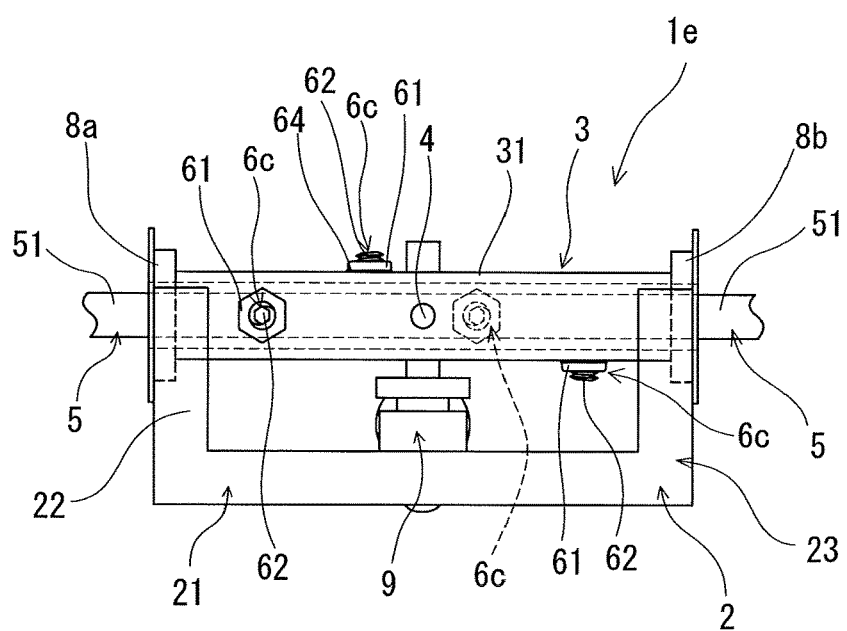
FIG. 15 is an enlarged front view of a holder-holding device of a blade tip-provided micropipette holding apparatus of another embodiment of the present invention.

In the micropipette holding apparatuses of the above-described all embodiments, the side hole, the female screw portion (nut), and the male screw portion may be formed like those of a micropipette holding apparatus 1e of an embodiment shown in FIG. 15. A holder position adjusting mechanism 6c of this embodiment is constructed of four side holes formed at different positions of the tubular body 31 in the axial direction thereof, male screw portions 62 constructing four holder position adjusting members, and four female screw portions 61 which are disposed in the vicinity of the side holes and engageable with the male screw portions 62 respectively.

In the micropipette holding apparatus 1e of this embodiment, the tubular body 31 is provided with four side holes formed by shifting them 90 degrees with respect to the central axis of the tubular body 31 toward the proximal end thereof in its axial direction. In other words, the four side holes are spirally disposed. Therefore the four side holes are not disposed at the same position of the tubular body 31 in its axial direction. In addition, a plurality of side holes is not arranged in a straight line in the axial direction of the tubular body. In the holder position adjusting mechanism 6c of this embodiment, holder position adjusting mechanisms (male screw member 62) located at odd-numbered positions from the left side in FIG. 15 are capable of adjusting longitudinal positions of the micropipette holder 5 inside the tubular body 31 through which the micropipette holder has been penetrated as shown in FIG. 15. The holder position adjusting mechanisms (male screw member 62) located at even-numbered positions from the left side are capable of adjusting vertical positions of the micropipette holder 5 inside the tubular body 31 through which the micropipette holder has been penetrated as shown in FIG. 15.

In the micropipette holding apparatuses of the above-described all embodiments, the tubular rotating member 3 is manually rotated by gripping the rotating operation projected portion 4. But the micropipette holding apparatus of the present invention is not limited thereto.

Figure 16:
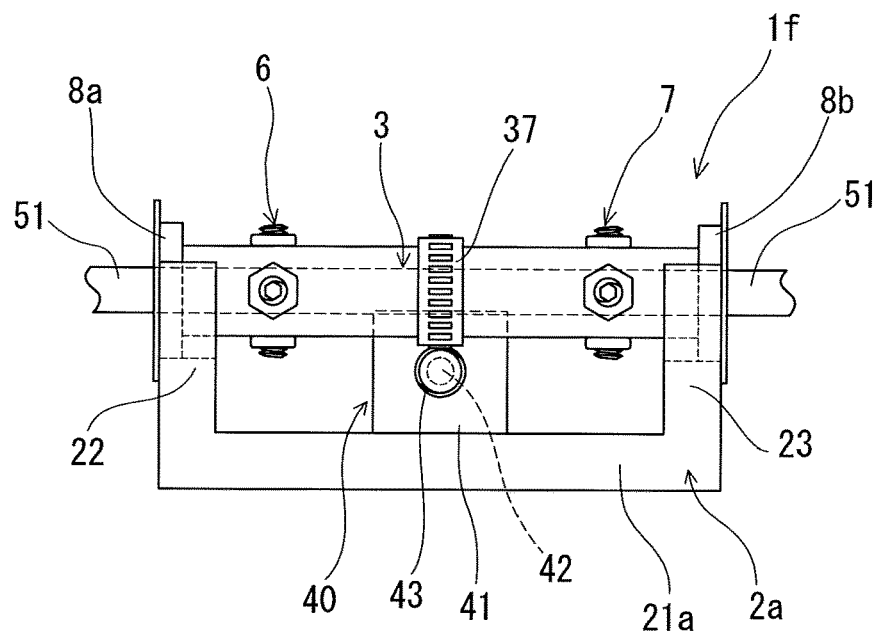
FIG. 16 is an enlarged front view of a holder-holding device of a blade tip-provided micropipette holding apparatus of another embodiment of the present invention
Figure 17:
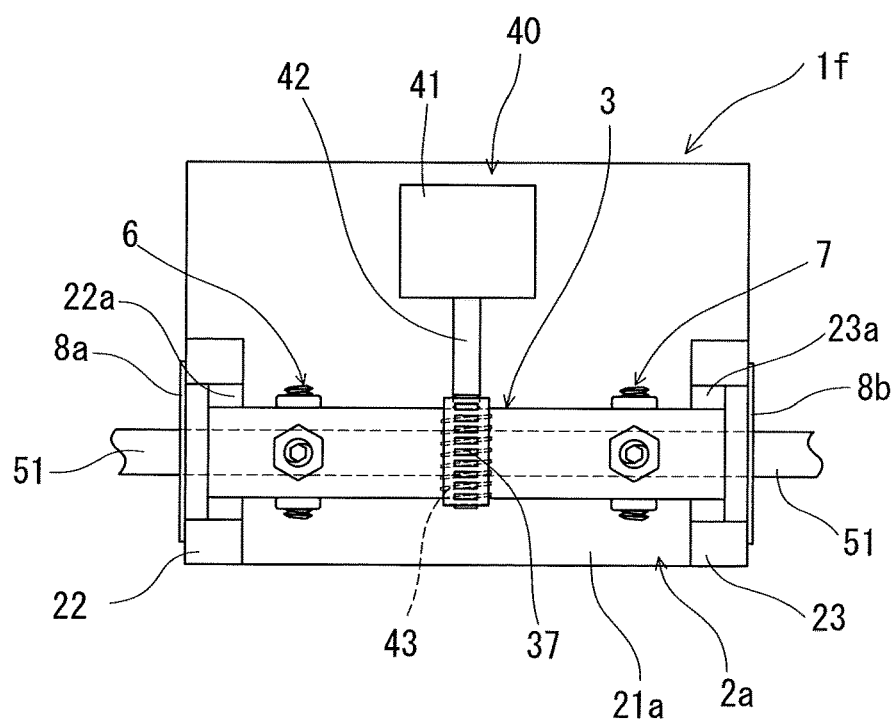
FIG. 17 is an enlarged plan view of the holder-holding device of the blade tip-provided micropipette holding apparatus shown in FIG. 16.
Figure 18:
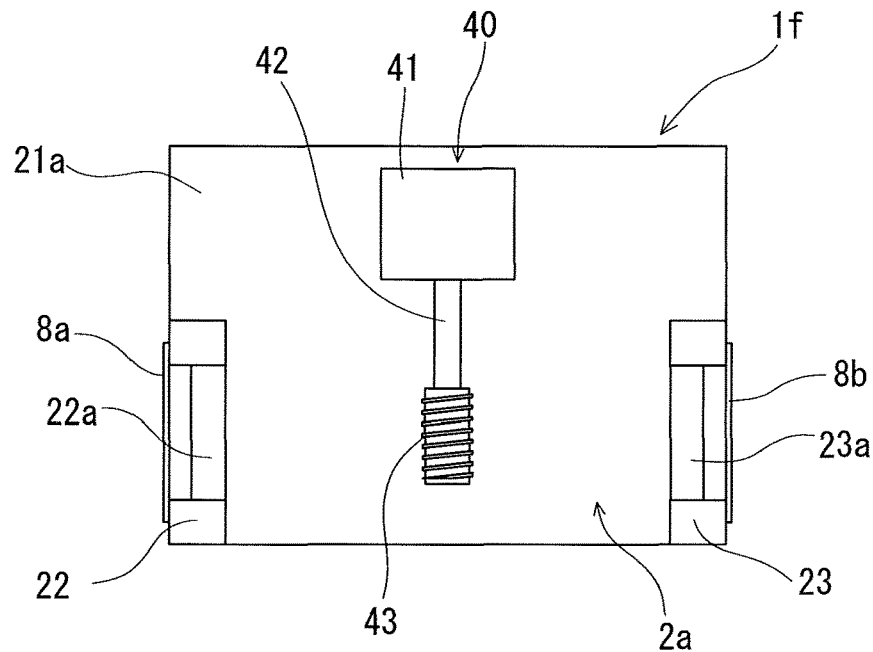
FIG. 18 is an enlarged plan view of a state in which a holder-holding device is removed from the blade tip-provided micropipette holding apparatus of FIG. 17.

Like a blade tip-provided micropipette holding apparatus if shown in FIGS. 16 through 18, the micropipette holding apparatus of the present invention may have a rotating means 40 for non-manually rotating the tubular rotating member 3.

As shown in FIG. 18, in the micropipette holding apparatus 1f of this embodiment, a base member 2a having a base portion 21a having a wide surface is used. A motor 41 is mounted on an upper surface of the base member 2a.

In the blade tip-provided micropipette holding apparatus 1f of this embodiment, the rotating means 40 has a rotational force transmitting part for transmitting the rotation of a rotating shaft 42 of a motor 41 to the tubular rotating member 3 so as to rotate the tubular rotating member 3. In this embodiment, the rotational force transmitting part is constructed of a worm gear 43 provided on the rotating shaft 42 of the motor 41 and a spur gear 37 provided on the tubular body 31 and engaging the worm gear 43. In combination of the worm gear 43 and the spur gear 37, the rotation of the rotating shaft of the motor 41 is altered by 90 degrees, which allows the tubular rotating member 3 to preferably rotate on its central axis. In combination of the worm gear 43 and the spur gear 37, the rotational speed of the rotating shaft 42 of the motor 41 is greatly reduced. Thus the tubular rotating member 3 is allowed to rotate slowly.

Figure 19:
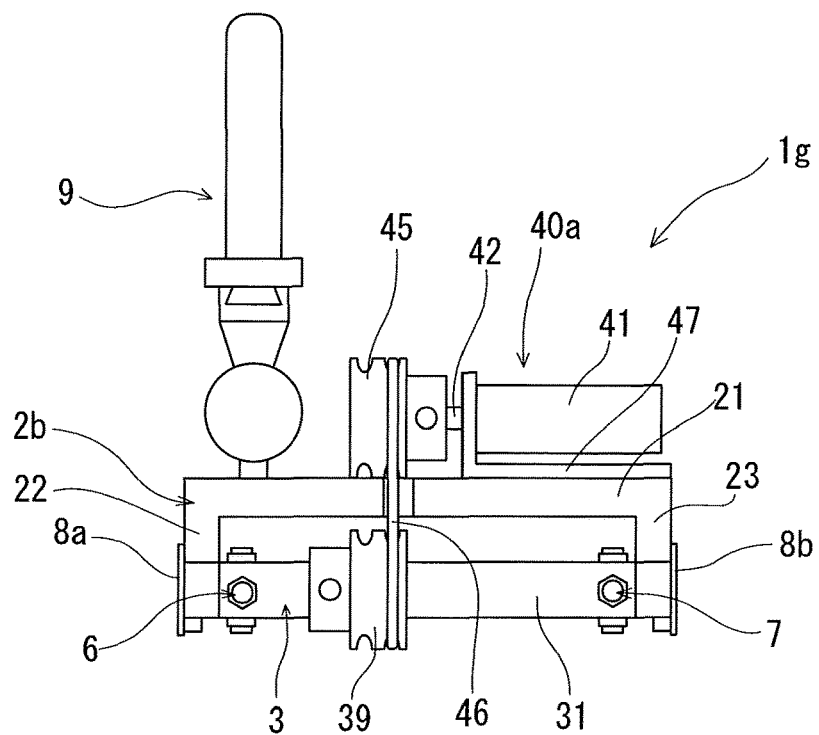
FIG. 19 is an enlarged front view of a holder-holding device of a blade tip-provided micropipette holding apparatus of another embodiment of the present invention.

The rotational force transmitting part may be constructed like the one provided for a rotating means 40a of a blade tip-provided micropipette holding apparatus 1g shown in FIG. 19. In the rotating means 40a of the micropipette holding apparatus 1g, pulleys and a belt are used as the rotational force transmitting part. More specifically, the rotational force transmitting part of the rotating means 40a is constructed of a first pulley 45 provided on the rotating shaft 42 of the motor 41, a second pulley 39 provided on the tubular body 31, and an annular belt (endless belt) 46 spanned between an annular concave portion of the first pulley 45 and that of the second pulley 39. In the apparatus 1g of this embodiment, the motor 41 is disposed parallel with the tubular rotating member 3. The rotating shaft of the motor 41 is also parallel with the tubular rotating member 3.

The first pulley 45 provided on the rotating shaft 42 of the motor 41 and the second pulley 39 provided on the tubular body 31 are also parallel with each other and adjacent to each other. The annular concave portion of the first pulley 45 and that of the second 39 pulley are adjacent to each other and located in a straight line. The annular belt (endless belt) 46 is spanned between the annular concave portions without loosening to couple the two pulleys 39, 45 to each other thereby. Caused by the rotation of the rotating shaft 42 of the motor 41, the pulley 45 rotates. The rotational force of the pulley 45 is transmitted to the pulley 39 through the belt 46. Thereby the rotating member 3 rotates preferably on its axis. A reduction gear for reducing the rotational speed of the rotating shaft may be mounted on the motor 41.

In the micropipette holding apparatus 1g of this embodiment, the rotating means 40a has a motor fixing member 47 fixed to the base portion 21 of the base member 20. The motor 41 is rotatably installed on the base member 20 by the fixing member 47.

Figure 20:
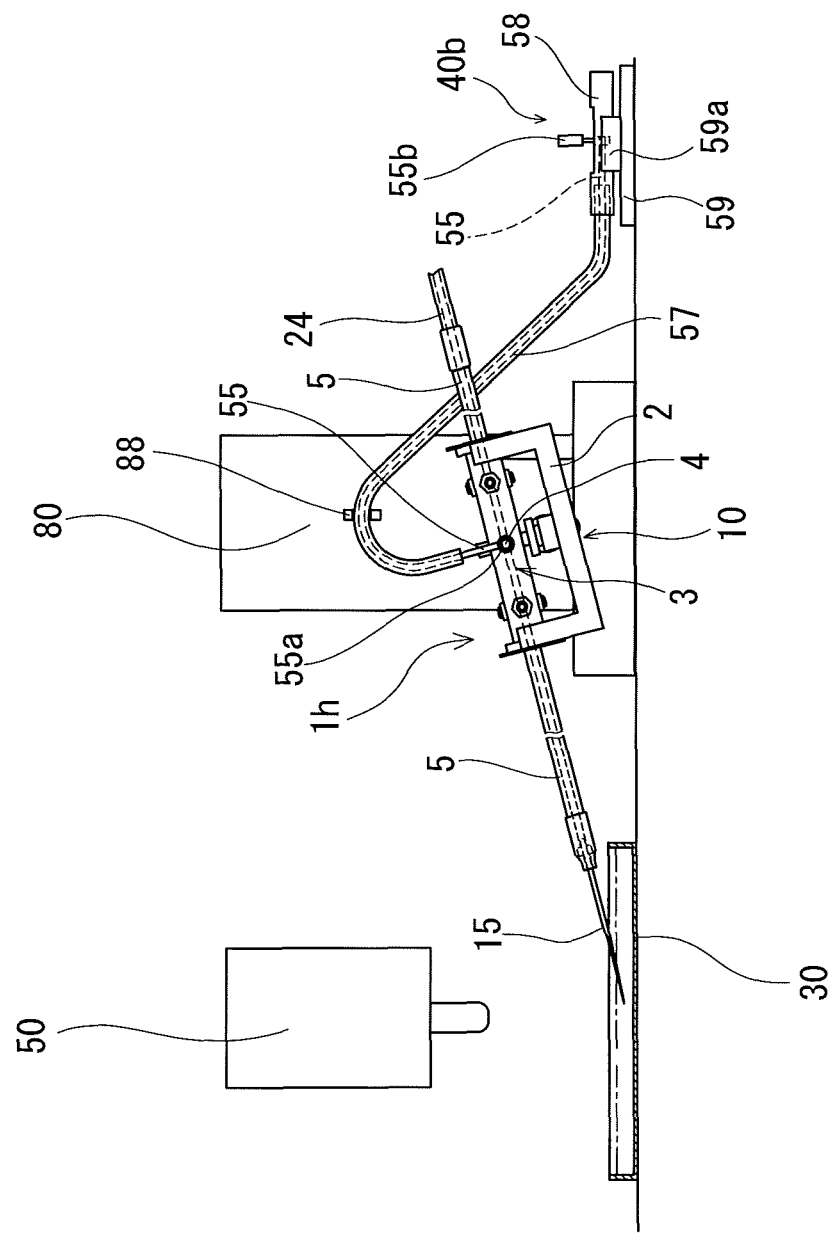
FIG. 20 is an explanatory view for explaining another embodiment of the blade tip-provided micropipette holding apparatus of the present invention.

Another embodiment of the blade tip-provided micropipette holding apparatus of the present invention shown in FIG. 20 is described below. A blade tip-provided micropipette holding apparatus 1h of this embodiment has a rotating mechanism 40b for manually rotating the tubular rotating member 3.

As shown in FIG. 20, the blade tip-provided micropipette holding apparatus 1h of this embodiment is incorporated in a sperm injecting manipulator 10. The sperm injecting manipulator 10 is mounted on a moving device 80 for moving the sperm injecting manipulator 10 in XYZ directions. Thus by driving the moving device 80, the sperm injecting manipulator 10 is capable of moving in longitudinal, left and right, and vertical directions. As shown in FIG. 20, when the blade tip-provided micropipette holding apparatus 1h is used, a petri dish 30 is disposed below a microscopic device 50.

As shown in FIG. 20, in this embodiment, the rotating mechanism 40b for manually rotating the tubular rotating member has a wire sheath 57 and an operation wire which slidably penetrates through the wire sheath 57. The operation wire 55 has a mounting portion 55a to be mounted on the rotating operation projected portion 4 on its front end. The wire 55 has a gripping portion (operation portion) 55b at its proximal-end portion. In this embodiment, the mounting portion 55a is formed of a ring-shaped member allowing the rotating operation projected portion 4 to penetrate therethrough. A tubular holding portion 58 is fixed to a proximal end of the wire sheath 57. Inside the tubular holding portion 58, the proximal-end portion of the wire 55 is projected from the sheath 57. The gripping portion 55b fixed to the proximal-end portion of the wire is projected beyond an axially extended slit formed on an upper surface of the tubular holding portion 58. Thus the operation portion 55b fixed to the rear end portion of the wire 55 is axially movable inside the slit of the tubular holding portion 58. By axially moving the operation portion 55b, the front end of the wire and the mounting portion 55a move back and forth. The longitudinal movement of the front end of the wire and that of the mounting portion 55a are transmitted to the rotating operation projected portion 4 on which the mounting portion 55a is mounted. Thereby the tubular rotating member 3 rotates.

More specifically, in a state shown in FIG. 20, when the operation portion 55b is moved leftward, the projected dimension of the wire 55 projected from the front end of the sheath 57 becomes long. As a result, the rotating operation projected portion 4 is pressed downward by the wire 55. Thereby the tubular rotating member 3 rotates downward. Conversely, when the operation portion 55b is moved rightward, the projected dimension of the wire 55 projected from the front end of the sheath 57 becomes short. As a result, the rotating operation projected portion 4 is pulled upward by the wire 55. Thereby the tubular rotating member 3 rotates upward.

As shown in FIG. 20, the rotating mechanism 40b of this embodiment for manually rotating the tubular rotating member has a base portion 59. The tubular holding portion 58 is fixed to the base portion 59 by a mounting portion 59a. In this embodiment, the sheath 57 is fixed to the moving device 80 by a fixing member 88. In this embodiment, the wire and the sheath are curvedly held by the fixing member 88. Thereby the direction in which the front-end portion of the wire and that of the sheath face is approximately orthogonal to the rotating shaft of the tubular rotating member 3. Thereby by subjecting the gripping portion 55b to a slide operation, the tubular rotating member 3 rotates preferably.

The intracytoplasmic sperm injection method of the present invention is described below with reference to FIGS. 21 through 23.

The intracytoplasmic sperm injection method of the present invention includes the step of holding an ovum 100 by a suction pipette 12; the step of bringing the front-end portion of the micropipette 15 having the blade tip 18 at its front end and accommodating a sperm therein into contact with the ovum held by the suction pipette 12; the step of moving the micropipette 15 forward and inserting the blade tip 18 into an egg zona pellucid 101; the step of bringing the blade tip 18 into contact with an egg membrane 102 of the ovum 100 and pressing the egg membrane 102 by means of the blade tip 18; the step of rotating the micropipette 15 on its central axis with its central axis being approximately centered in the rotation thereof to rotate the blade surface of the blade tip 18 so that the blade tip 18 pierces through the egg membrane 102 and enters into a cytoplasm 103; and the step of releasing the sperm accommodated inside the micropipette 15 in an interior of the cytoplasm 103.

The steps to be executed in the intracytoplasmic sperm injection method of the present invention are described in detail below.

As shown in FIG. 21, the petri dish 30 accommodating the ovum 100 together with a culture liquid is prepared. A petri dish 30 is placed below a microscopic device 50. At one side of the petri dish 30, the sperm injecting manipulator 10 incorporating the micropipette holding apparatus 1 of the present invention holding the blade tip-provided micropipette 15 accommodating the sperm is disposed. At the other side of the petri dish 30, an ovum-holding manipulator 25 incorporating the micropipette holding apparatus holding the suction pipette 12 is disposed.

In the system shown in FIG. 21, the sperm injecting manipulator 10 is mounted on the moving device 80 for moving the sperm injecting manipulator 10 in the XYZ directions. Therefore by driving the moving device 80, the sperm injecting manipulator 10 is capable of moving in longitudinal, left and right, and vertical directions.

Similarly to the above, the ovum-holding manipulator 25 is mounted on a moving device 90 for moving the ovum-holding manipulator 25 in the XYZ directions. Therefore by driving the moving device 90, the ovum-holding manipulator 25 is capable of moving in longitudinal, left and right, and vertical directions. The ovum-holding manipulator 25 has a suction pipette holder 26 and a holder-holding member 29 mounted on the moving device 90. The suction pipette holder 26 has the same construction as that of the micropipette holder 5. More specifically, the suction pipette holder 26 has a front-end member 27 for holding the suction pipette 12 at its front end and a proximal-end member 28 for holding the tube 60.

Figure 22A:
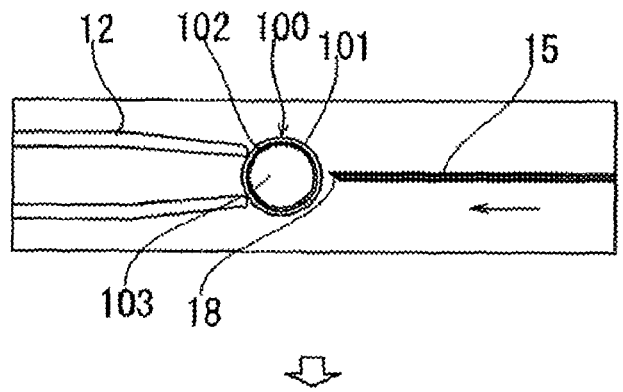
FIGS. 22A-C is an explanatory view for explaining the intracytoplasmic sperm injection method of the present invention.

In the intracytoplasmic sperm injection method of the present invention, as shown in FIGS. 21 and 22(A), initially, the step of sucking and holding the ovum 100 by the suction pipette 12 is executed. At this step, the moving device 90 is operated to insert the suction pipette 12 held by the ovum-holding manipulator 25 into the petri dish 30 where the ovum 100 is accommodated together with the culture liquid. Thereafter a sucking means (not shown) connected to the ovum-holding manipulator 25 is operated to suck the ovum 100 and hold it at the front end of the suction pipette 12.

Figure 22B:
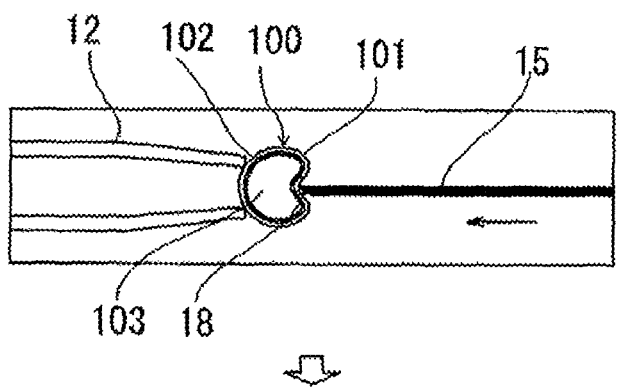

The step to be executed thereafter is to bring the front-end portion of the micropipette 15 having the blade tip 18 at its front end and accommodating the sperm therein into contact with the ovum held by the suction pipette 12. At this step, the moving device 80 is operated to insert the blade tip-provided micropipette 15, accommodating the sperm, which is held by the sperm injecting manipulator 10 into the petri dish 30 to approach the blade tip 18 proximately to the ovum 100, as shown in FIG. 22(A). Thereafter the moving device 80 is operated to slightly move the blade tip-provided micropipette 15 toward the ovum to bring the blade tip 18 of the micropipette 15 into contact with the ovum, as shown in FIG. 22(B). Caused by the contact between the blade tip 18 and the ovum, the ovum deforms, i.e., becomes slightly hollow.

Figure 22C:
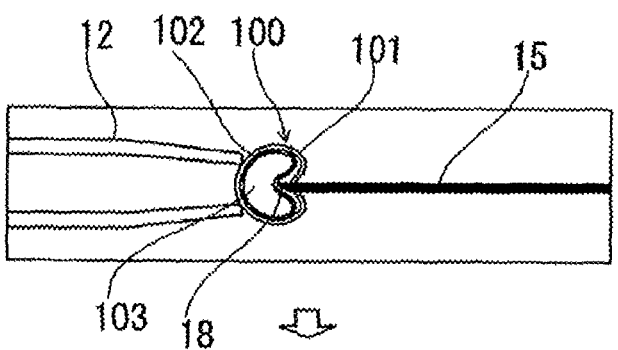

The step to be executed thereafter is to move the micropipette 15 forward so that the blade tip 18 pierces through the egg zona pellucid 101. At this step, as shown in FIG. 22(C), the moving device 80 is operated so that the blade tip 18 of the blade tip-provided micropipette 15 pierces into the ovum 100 and pierces through the egg zona pellucid 101.

The step to be executed thereafter is to bring the blade tip 18 into contact with the egg membrane 102 of the ovum 100 and pressing the egg membrane 102 by means of the blade tip 18. At this step, the moving device 80 is operated to slightly move the blade tip-provided micropipette 15 forward toward the ovum. Upon completion of the step at which the blade tip 18 pierces through the egg zona pellucid 101 of the ovum, there is a case in which the egg membrane 102 is naturally pressed by the blade tip 18. Even in the case in which the egg membrane 102 is naturally pressed by the blade tip 18, the moving device 80 may be operated to slightly move the blade tip-provided micropipette 15 toward the ovum so that the blade tip presses the egg membrane to a higher extent. By executing this step, as shown in FIG. 22(C), the blade tip 18 of the blade tip-provided micropipette 15 pierces through the egg zona pellucid 101 and presses the egg membrane 102, and the egg membrane 102 is deformed by the pressing of the blade tip 18 against it.

Figure 23D:
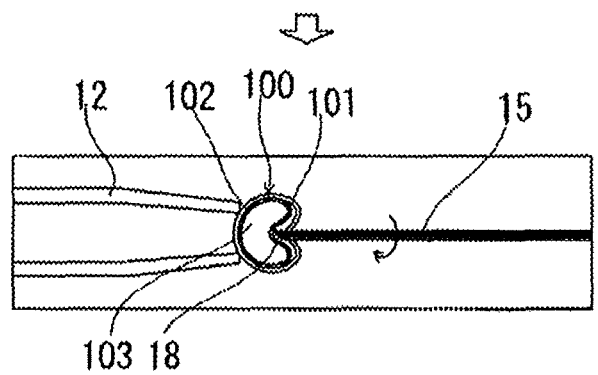
FIGS. 23D-F is an explanatory view for explaining the intracytoplasmic sperm injection method of the present invention.

As shown in FIG. 23(D), the step to be executed thereafter is to rotate the micropipette 15 on its central axis with its central axis being approximately centered to rotate the blade surface of the blade tip 18 so that the blade tip 18 pierces through the egg membrane 102 and enters into the cytoplasm 103.

Figure 23E:
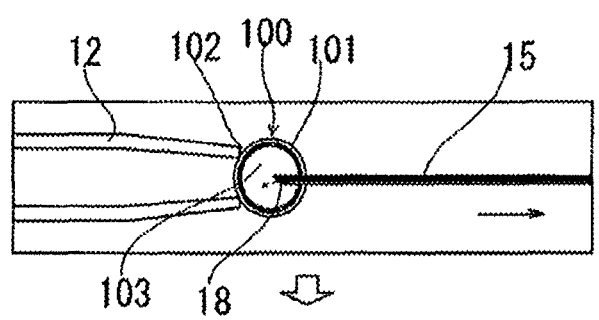
Figure 23F:
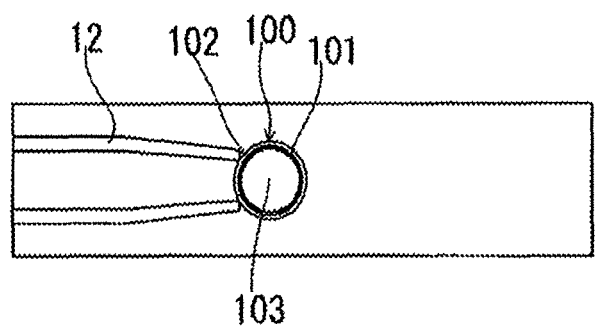

This rotation step is executed not by altering the position of the micropipette 15, but by moving the rotating operation projected portion 4 of the tubular rotating member 3 of the micropipette holding apparatus 1 of the present invention upward or downward. By executing this step, owing to the rotation of the blade surface of the blade tip 18, the blade tip 18 pierces through the egg membrane 102. Thereby as shown in FIG. 23(E), the blade tip 18 enters into the cytoplasm 103. This micropipette rotation step may be executed with the blade tip-provided micropipette 15 being slightly moved toward the ovum.

At the step of rotating the micropipette, it is preferable to rotate the micropipette on the central axis of the front-end portion thereof with the central axis of the front-end portion thereof being approximately centered. In other words, it is preferable to use the blade tip-provided micropipette 15 in a state in which the micropipette accommodating the sperm is held by the micropipette 15 in such a way that the micropipette is rotated on the central axis of the front-end portion of the micropipette with the central axis of its front-end portion being approximately centered.

As shown in FIG. 23(E), the step to be executed thereafter is to release the sperm accommodated inside the micropipette 15 in the interior of the cytoplasm 103. This step is executed by operating a discharge means (not shown) connected to the sperm injecting manipulator 10 so that the sperm is discharged from the micropipette 15.

After the sperm injection step finishes, the moving device 80 is operated to move the blade tip-provided micropipette 15 rearward to withdraw it from the ovum 100. Thereby the intracytoplasmic sperm injection method finishes. Inside the petri dish 30, the ovum into which the sperm has been injected is sucked by the suction pipette 12 and held thereby.

INDUSTRIAL APPLICABILITY

The blade tip-provided micropipette holding apparatus of the present invention is as described below.
(1) A blade tip-provided micropipette holding apparatus comprising a tubular micropipette holder so constructed that a blade tip-provided micropipette to be inserted into a living cell can be mounted on a front-end portion thereof and a holder-holding device for holding said micropipette holder; wherein said holder-holding device has a base member and a tubular rotating member which is rotatably held by said base member and into which said micropipette holder can be penetrated; and said tubular rotating member has a holder position adjusting mechanism comprising a plurality of side holes formed on a side surface of said tubular rotating member at different positions in a circumferential direction thereof and holder position adjusting members each capable of entering into said tubular rotating member from said side holes and contacting an outer surface of said micropipette holder penetrating through said tubular rotating member.

Because the blade tip-provided micropipette holding apparatus rotatably holds the tubular micropipette holder on which the blade tip-provided micropipette to be pierced into the living cell can be mounted, in performing the operation of inserting the blade tip-provided micropipette into the cell, it is possible to easily the operation of rotating the blade tip-provided micropipette and thus insert the blade tip of the micropipette into the cell. In addition, in the blade tip-provided micropipette holding apparatus, the tubular rotating member through which the micropipette holder is penetrated has the holder position adjusting member. Thus it is possible to adjust the center of the tubular rotating member during the rotation thereof. In other words, because it is possible to adjust the rotation center of the blade tip of the blade tip-provided micropipette mounted on the micropipette holder, the blade tip-provided micropipette can be rotated in a favorable state.

The above-described embodiments may be as described below.
(2) A blade tip-provided micropipette holding apparatus according to the above (1), wherein by adjusting said holder position adjusting mechanisms with said micropipette being mounted on said micropipette holder, a central axis of a front-end portion of said micropipette can be adjusted to be approximately centered during a rotation of said tubular rotating member.
(3) A blade tip-provided micropipette holding apparatus according to the above (1) or (2), wherein said holder position adjusting mechanism comprises said side holes, male screw members each constituting said holder position adjusting member, and female screw portions which are formed in a vicinity of said side holes or inside said side holes and threadedly engageable with said male screw members respectively.
(4) A blade tip-provided micropipette holding apparatus according to any one of the above (1) through (3), wherein said tubular rotating member has an operation projected portion for manually rotating said tubular rotating member.
(5) A blade tip-provided micropipette holding apparatus according to any one of the above (1) through (3), having a rotating means for non-manually rotating said tubular rotating member.
(6) A blade tip-provided micropipette holding apparatus according to the above (5), wherein said rotating means comprises a motor and a rotational force transmitting mechanism for coupling a rotating shaft of said motor and said tubular rotating member to each other and rotating said tubular rotating member by a rotation of said rotating shaft.
(7) A blade tip-provided micropipette holding apparatus according to any one of the above (1) through (6), wherein said base member has a base portion and two side plate portions erect from said base portion; said tubular rotating member has ball bearings provided at both ends thereof; and said tubular rotating member is rotatably held by said base member by being fixed to said two side plate portions through said ball bearings.
(8) A blade tip-provided micropipette holding apparatus according to any one of the above (1) through (7), wherein said tubular rotating member has two elastic tubular members accommodated inside one end side and other end side thereof; and said elastic tubular members are capable of closely contacting said micropipette holder and allow said micropipette holder to be penetrated therethrough.

(9) A blade tip-provided micropipette holding apparatus according to any one of the above (1) through (8), wherein said tubular rotating member has a first holder position adjusting mechanism and a second holder position adjusting mechanism spaced at a predetermined interval from said first holder position adjusting mechanism.

(10) A blade tip-provided micropipette holding apparatus according to any one of the above (1) through (9), wherein said holder position adjusting mechanism comprises a plurality of said side holes formed opposite to each other or at intervals of an equal angle with respect to a central axis of said tubular rotating member and holder position adjusting members each capable of entering into said tubular rotating member from said side holes and contacting an outer surface of said micropipette holder penetrating through said tubular rotating member.

(11) A blade tip-provided micropipette holding apparatus according to any one of the above (1) through (10), wherein said micropipette holding apparatus has a mounting part which is mounted on said base member and used to install said micropipette holding apparatus on a manipulator apparatus.

(12) A blade tip-provided micropipette holding apparatus according to any one of the above (1) through (11), wherein said micropipette holder has a tubular main body, a front-end side ring-shaped member provided at a front-end portion of said tubular main body, a proximal-end side ring-shaped member provided at a proximal-end side of said tubular main body, and a tubular elastic member accommodated inside said front-end side ring-shaped member and pressed by said front-end side ring-shaped member and said front end of said tubular main body; and said tubular elastic member allows a proximal-end portion of said micropipette to be penetrated therethrough and is capable of holding said proximal-end portion of said micropipette when said tubular elastic member is pressed.

(13). A blade tip-provided micropipette holding apparatus according to any one of the above (1) through (12), which holds a micropipette for use in microinsemination.

The intracytoplasmic sperm injection method of the present invention is as described below.

(14) An intracytoplasmic sperm injection method comprising a step of holding an ovum by a suction pipette; a step of bringing a front-end portion of a micropipette having a blade tip at a front end thereof and accommodating a sperm therein into contact with an ovum held by said suction pipette; a step of moving said micropipette forward and inserting said blade tip into an egg zona pellucid; a step of bringing said blade tip into contact with an egg membrane of said ovum and pressing said egg membrane by means of said blade tip; a step of rotating said micropipette to rotate a blade surface of said blade tip so that said blade tip pierces through said egg membrane and enters into a cytoplasm; and a step of releasing said sperm accommodated inside said micropipette in an interior of said cytoplasm.

In the present invention, by rotating the blade surface of the blade tip of the micropipette, it is possible to allow the blade tip to enter into the egg membrane and the cytoplasm securely and easily. Thus it is possible to allow the blade tip of the micropipette to reliably reach into the cytoplasm.

The above-described embodiments may be as described below.

(15) An intracytoplasmic sperm injection method according to the above (14), wherein said micropipette is rotated with a central axis of said front-end portion thereof being approximately centered.

The invention claimed is:

1. A blade tip-provided micropipette holding apparatus comprising,
a tubular micropipette holder and a holder-holding device for holding said micropipette holder;
wherein said tubular micropipette holder is constructed that a blade tip-provided micropipette can be mounted on a front-end portion thereof;
said holder-holding device has a base member and a tubular rotating member which is rotatably held by said base member and into which said tubular micropipette holder can be penetrated; and
said tubular rotating member has a holder position adjusting mechanism comprising a plurality of side holes formed on a side surface of said tubular rotating member at different positions in a circumferential direction thereof and holder position adjusting members each capable of entering into said tubular rotating member from said side holes and contacting an outer surface of said micropipette holder penetrating through said tubular rotating member;
wherein said base member has a base portion and two side plate portions erect from said base portion; said tubular rotating member has ball bearings provided at both ends thereof; and said tubular rotating member is rotatably held by said base member by being fixed to said two side plate portions at said ball bearings.

2. A blade tip-provided micropipette holding apparatus according to claim 1, wherein by adjusting said holder position adjusting mechanisms with said micropipette being mounted on said micropipette holder, a central axis of a front-end portion of said micropipette can be adjusted to be approximately centered during a rotation of said tubular rotating member.

3. A blade tip-provided micropipette holding apparatus according to claim 1, wherein said holder position adjusting mechanism comprises said side holes, male screw members each constituting said holder position adjusting member, and female screw portions which are formed in a vicinity of said side holes or inside said side holes and threadedly engageable with said male screw members respectively.

4. A blade tip-provided micropipette holding apparatus according to claim 1, wherein said tubular rotating member has an operation projected portion for manually rotating said tubular rotating member.

5. A blade tip-provided micropipette holding apparatus according to claim 1, having a rotating device for non-manually rotating said tubular rotating member.

6. A blade tip-provided micropipette holding apparatus according to claim 5, wherein said rotating device comprises a motor and a rotational force transmitting mechanism for coupling a rotating shaft of said motor and said tubular rotating member to each other and rotating said tubular rotating member by a rotation of said rotating shaft.

7. A blade tip-provided micropipette holding apparatus according to claim 1, wherein said tubular rotating member has two elastic tubular members accommodated inside one end side and other end side thereof; and said elastic tubular members are capable of closely contacting said micropipette holder and allow said micropipette holder to be penetrated therethrough.

8. A blade tip-provided micropipette holding apparatus according to claim 1, wherein said tubular rotating member has a first holder position adjusting mechanism and a second holder position adjusting mechanism spaced at a predetermined interval from said first holder position adjusting mechanism.

9. A blade tip-provided micropipette holding apparatus according to claim 1, wherein said holder position adjusting mechanism comprises a plurality of said side holes formed opposite to each other or at intervals of an equal angle with respect to a central axis of said tubular rotating member and holder position adjusting members each capable of entering into said tubular rotating member from said side holes and contacting an outer surface of said micropipette holder penetrating through said tubular rotating member.

10. A blade tip-provided micropipette holding apparatus according to claim 1, wherein said micropipette holding apparatus has a mounting part which is mounted on said base member and used to install said micropipette holding apparatus on a manipulator apparatus.

11. A blade tip-provided micropipette holding apparatus according to claim 1, wherein said micropipette holder has a tubular main body, a front-end side ring-shaped member provided at a front-end portion of said tubular main body, a proximal-end side ring-shaped member provided at a proximal-end side of said tubular main body, and a tubular elastic member accommodated inside said front-end side ring-shaped member and pressed by said front-end side ring-shaped member and said front end of said tubular main body; and said tubular elastic member allows a proximal-end portion of said micropipette to be penetrated therethrough and is capable of holding said proximal-end portion of said micropipette when said tubular elastic member is pressed.

12. A blade tip-provided micropipette holding apparatus according to claim 1, which holds a micropipette for use in microinsemination.

* * * * *